(12) United States Patent
Kroll et al.

(10) Patent No.: US 7,158,825 B1
(45) Date of Patent: Jan. 2, 2007

(54) IMPLANTABLE CARDIOVERTER DEFIBRILLATOR WITH LEAKAGE DETECTION AND PREVENTION SYSTEM

(75) Inventors: Mark W. Kroll, Simi Valley, CA (US); Gabriel A. Mouchawar, Valencia, CA (US); Geroge I. Isaac, Port Hueneme, CA (US)

(73) Assignee: Pacesetter, inc., Sylmar, CA (US)

( * ) Notice: Subject to any disclaimer, the term of this patent is extended or adjusted under 35 U.S.C. 154(b) by 507 days.

(21) Appl. No.: 10/373,236

(22) Filed: Feb. 24, 2003

(51) Int. Cl.
*A61N 1/39* (2006.01)

(52) U.S. Cl. .............................................. 607/5; 607/4
(58) Field of Classification Search .................. 607/4, 607/5, 8, 9, 33, 34
See application file for complete search history.

(56) References Cited

U.S. PATENT DOCUMENTS

| | | | |
|---|---|---|---|
| 5,163,428 A | 11/1992 | Pless | 128/419 D |
| 5,472,454 A | 12/1995 | Ozawa | 607/5 |
| 5,591,211 A * | 1/1997 | Meltzer | 607/5 |
| 5,658,319 A * | 8/1997 | Kroll | 607/7 |
| 5,899,923 A * | 5/1999 | Kroll et al. | 607/5 |
| 6,096,062 A * | 8/2000 | Silvian | 607/5 |
| 6,898,463 B1 * | 5/2005 | Dropps et al. | 607/27 |

FOREIGN PATENT DOCUMENTS

EP 0480569 A3 8/1991

* cited by examiner

*Primary Examiner*—Robert Pezzuto
*Assistant Examiner*—Yun Haeng Lee

(57) ABSTRACT

A leakage detection system for use in an implantable cardiac stimulation device, such as an implantable cardioverter defibrillator. The leakage detection system employs one or more switches capable of disconnecting leaky electronic components from the power cell of the stimulation device, and of measuring electric currents to various components of this device. The leakage detection system includes a plurality of switches that are connected between selected components of the ICD, such as high-voltage capacitors, and the power cell. The switches can be selectively activated to disconnect the leaky or faulty components from the power cell, thereby preventing leakages from these components.

8 Claims, 5 Drawing Sheets

IMPLANTABLE CARDIOVERTER DEFIBRILLATOR WITH LEAKAGE DETECTION AND PREVENTION SYSTEM

FIELD OF THE INVENTION

The present invention generally relates to implantable cardiac stimulation devices such as implantable cardioverter defibrillators. More particularly, the present invention relates to an implantable cardioverter defibrillator equipped with a leakage detection system that isolates possible leaky electronic components from the power cell.

BACKGROUND OF THE INVENTION

In the normal human heart, the sinus node, that is generally located near the junction of the superior vena cava and the right atrium, constitutes the primary natural pacemaker initiating rhythmic electrical excitation of the heart chambers. Disruption of the heart's natural pacemaker and conduction system, as a result of aging and/or disease, can be successfully treated using various implantable cardiac stimulation devices, including pacemakers and implantable cardioverter defibrillators. A pacemaker is generally arranged to deliver rhythmic electrical pulses to the heart to maintain a normal rhythm in patients having bradycardia, which is too slow of heart rate, or other conduction abnormalities. In contrast, an implantable cardioverter defibrillator, commonly referred to as an "ICD", can recognize tachycardia and/or fibrillation and deliver electrical therapy in order to terminate such arrhythmias. In addition, such ICDs may often be configured to perform pacemaking functions (or pacing) as well.

Depending upon patients' needs, the ICDs generate pacing, cardioverting, and/or defibrillating pulses, and deliver them to excitable cardiac tissues of the patients' heart through electrical leads and electrodes. Difficulties arise when one or more electronic components of the ICDs leak currents and dissipate energy. The leaky components drain electric power from the power cells of the ICDs, resulting in the generation of electrical shocks with voltages or currents less than that required to remedy the ailing hearts. The premature power depletion may cause early retirement of the ICDs. In addition, the controllers of the ICDs and other components may malfunction due to weak power supply, and may eventually lead to dangerous conditions.

The problematic components of the current ICDs include decoupling capacitors that are connected to the power cells. In general, these decoupling capacitors are connected in parallel with the power cells to provide a relatively constant current and voltage. However, the decoupling capacitors may not be as reliable as expected. Many times, such capacitors exhibit partial shorts, deplete the power cells, and significantly reduce the longevity of the ICDs.

The ICD may monitor the electric voltage or current to its components, in order to detect the current leakage. However, the measured voltage or current might not identify the source of such leakage, because conventional current meters measure only the electric current supplied to all the circuits of the ICD.

In addition, because the current leakage in an ICD is unpredictable, the ICD undergoes a long hold period after it is manufactured to measure the voltage of the power cells and to estimate the leakage current. Such a process is not only inconvenient but also uneconomical. Furthermore, such a process might not detect less severe current leakages in the decoupling capacitors.

Therefore, it would be desirable to provide a leakage detection and prevention system for use in an ICD, with the ability to readily detect current leakages and to prevent, or at least minimize, the leakage by, for example, isolating leaky electronic components from the power cells.

SUMMARY

The present invention addresses the above need by providing an implantable stimulation device, such as an implantable cardioverter defibrillator (ICD) which is equipped with a leakage detection system to assess current leakages from the leaky components. The leakage detection system employs one or more switches capable of disconnecting the leaky electronic components from the power cell (or cells) of the ICD, and of measuring electric currents to various components of the ICD.

The leakage detection system includes a plurality of switches that are connected between selected components of the ICD, such as high-voltage capacitors, and the power cell. The switches can be selectively activated to disconnect the components from the power cell, thereby preventing leakages from leaky or faulty components.

In one embodiment, at least one of the switches is an ON-OFF switch, preferably a field effect transistor, having an ON-resistance ranging up to about 0.1 ohm and more particularly from 0.01 ohm to 0.09 ohm. The switch is disposed between the component and power cell, e.g., between one end of the power cell and that of the component. The switch can be disposed between the power cell and a ground node, or between the component and the ground node.

The cardiac stimulation device includes a controller that regulates the operation of the switch. For example, the controller opens the switch during pacing and/or sensing operations of the stimulation device, and closes it only during application of high-voltage shock pulses to the heart. The controller opens the switch again after the application of the high-voltage shock pulses to the heart.

The foregoing features of the present invention are also realized by a leakage detection system capable of detecting a current leakage from a capacitor that is connected in parallel with the power cell. A voltage converter of the stimulation device is connected to the power cell and the capacitor in parallel, and converts a low voltage input pulse from the power cell to a high voltage output pulse. The low-voltage components sense physiological conditions of the heart and/or stimulate the heart, while the high-voltage components generate and deliver high-voltage shock pulses to the heart.

In one embodiment, the leakage detection system includes a low-voltage current path connecting the power cell directly to the low-voltage components of the stimulation device, a first switch disposed between the capacitor and the power cell, a high-voltage current path connecting the power cell to the high-voltage component through the first switch, a second switch disposed between the capacitor and the high-voltage parts along the high-voltage current path, and a resistor disposed between the high-voltage and low-voltage paths to interconnect these paths.

In another embodiment, the leakage detection system includes a diode connected in parallel with the component to be tested, to connect the high- and low-voltage paths. The leakage detection system may also include a filter with a filter resistor disposed along the low-voltage path, and a filter capacitor connected between the high- and low-voltage paths.

BRIEF DESCRIPTION OF THE DRAWINGS

Various features of the present invention and the manner of attaining such will now be described in greater detail with reference to the following description, claims, and drawings, wherein reference numerals are reused when appropriate, to indicate a correspondence between the referenced items, and wherein:

DETAILED DESCRIPTION OF PREFERRED EMBODIMENTS

The following description is of a best mode presently contemplated for practicing the present invention. This description is not to be taken in a limiting sense but is made merely for the purpose of describing the general principles of the invention. In the description of the invention that follows, like numerals or reference designators will be used to refer to like parts or elements throughout. The present invention is directed at providing various leakage prevention and detection systems for implantable cardiac stimulating devices which possess pacemaking, cardioversion, and/or defibrillation capabilities.

A cardiac stimulation device 10 will be described in conjunction with FIGS. 1 and 2, in which the features included in this invention could be implemented. It is recognized, however, that numerous variations of such a device exist in which various methods included in the present invention can be implemented without deviating from the scope of the present invention.

Figure 1:
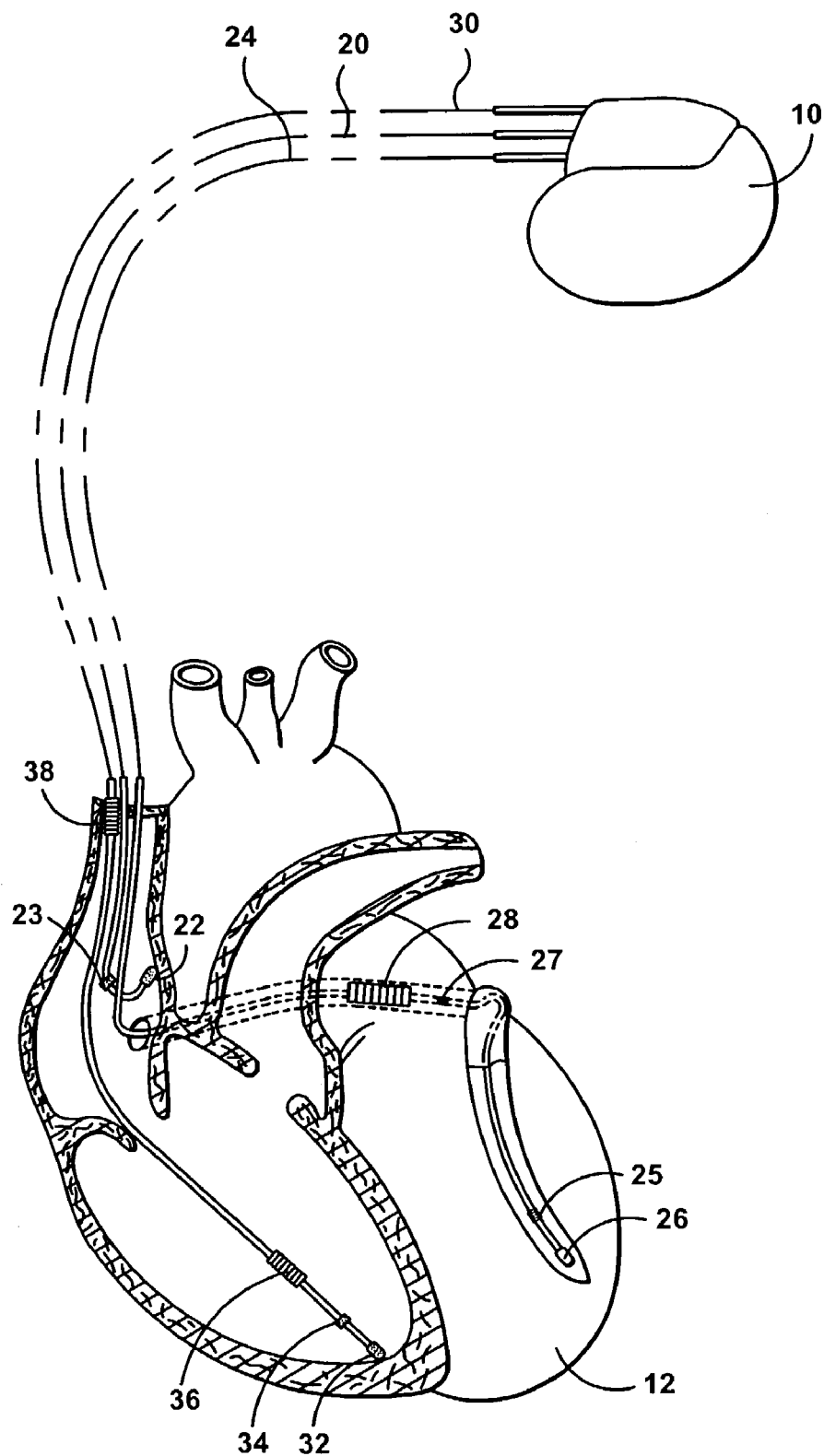
FIG. 1 is a simplified, partly cut-away view of an exemplary implantable cardiac stimulation device in electrical communication with at least three leads implanted into a patient's heart for delivering multi-chamber stimulation and shock therapy according to the present invention.

FIG. 1 illustrates the stimulation device 10 in electrical communication with a patient's heart 12 by way of three leads 20, 24 and 30 suitable for delivering multi-chamber stimulation and/or shock therapy. To sense atrial cardiac signals and to provide right atrial chamber stimulation therapy, the device 10 is coupled to an implantable right atrial lead 20 including at least one atrial tip electrode 22 that typically is implanted in the patient's right atrial appendage. The right atrial lead 20 may also include an atrial ring electrode 23 to allow bipolar stimulation or sensing in combination with the atrial tip electrode 22.

To sense the left atrial and left ventricular cardiac signals and to provide left-chamber stimulation therapy, the stimulation device 10 is coupled to a "coronary sinus" lead 24 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and/or ventricular cardiac signals; deliver left ventricular pacing therapy using at least one left ventricular tip electrode 26 for unipolar configurations or in combination with left ventricular ring electrode 25 for bipolar configurations; deliver left atrial pacing therapy using at least one left atrial ring electrode 27 as well as shocking therapy using at least one left atrial coil electrode 28.

The stimulation device 10 is also shown in electrical communication with the patient's heart 12 by way of an implantable right ventricular lead 30 including, in this embodiment, a right ventricular (RV) tip electrode 32, a right ventricular ring electrode 34, a right ventricular coil electrode 36, a superior vena cava (SVC) coil electrode 38, and so on. Typically, the right ventricular lead 30 is inserted transvenously into the heart 12 so as to place the right ventricular tip electrode 32 in the right ventricular apex such that the RV coil electrode 36 is positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
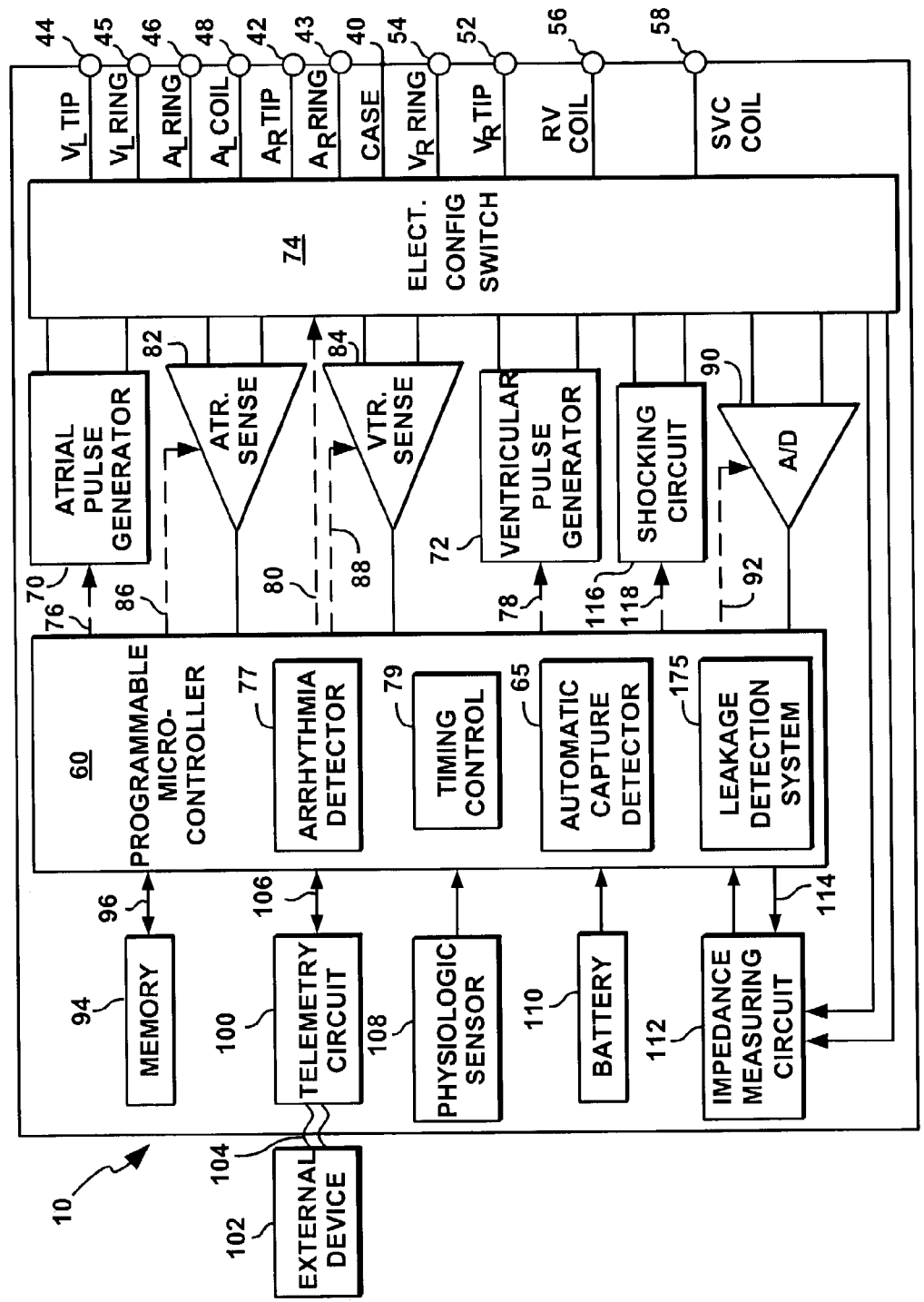
FIG. 2 is a functional block diagram of the exemplary implantable cardiac stimulation device of FIG. 1, illustrating the basic elements providing pacing stimulation, cardioversion, and defibrillation in four chambers of the heart according to the present invention.

FIG. 2 illustrates a simplified block diagram of the multi-chamber implantable stimulation device 10, which is capable of treating both fast arrhythmia and slow arrhythmia with stimulation therapy, including cardioversion, defibrillation, and pacing stimulation. While a particular multi-chamber device is shown, this is for illustration purposes only, and one of ordinary skill in the pertinent art could readily duplicate, eliminate or disable the appropriate circuitry in any desired combination to provide a device capable of treating the appropriate chamber(s) with cardioversion, defibrillation, and/or pacing stimulation.

The stimulation device 10 includes a housing 40 which is often referred to as "can," "case," or "case electrode," and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 further includes a connector having a plurality of terminals 42, 43, 44, 45, 46, 48, 52, 54, 56, and 58 (shown schematically and, for convenience, the names of the electrodes to which they are connected are shown next to corresponding terminals). As such, in order to achieve right atrial sensing and stimulation, the connector includes at least one right atrial tip terminal (AR TIP) 42 adapted for connection to the atrial tip electrode 22. The connector may also include a right atrial ring terminal (AR RING) 43 for connection to the right atrial ring electrode 23.

To achieve left chamber sensing, pacing, and/or shocking, such a connector includes a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, that are adapted for connection to the left ventricular tip electrode 26, the left ventricular ring electrode 25, the left atrial ring electrode 27, and the left atrial coil electrode 28, respectively.

To support right ventricular sensing, pacing, and/or shocking, the connector may further include a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular (RV) tip electrode 32, the RV ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may include RAM or ROM memory, logic and timing circuitry, state machine circuitry, and/or I/O circuitry. Typically, the microcontroller 60 may have the ability to process or monitor various input signals (data) as controlled by a program code stored in a designated block of memory.

FIG. 2 illustrates an atrial pulse generator 70 and ventricular pulse generator 72 which generate stimulation pulses for delivery by the right atrial lead 20, the right ventricular lead 30, and/or the coronary sinus lead 24 via a switch 74. It is understood that, to provide the stimulation therapy in each of the four chambers of the heart, the atrial pulse generator 70 and the ventricular pulse generator 72 may include, e.g., dedicated pulse generators, independent pulse generators, multiplexed pulse generators, and/or shared pulse generators. The atrial pulse generator 70 and the ventricular pulse generator 72 are generally controlled by the microcontroller 60 via appropriate control signals 76 and 78, respectively, to trigger or inhibit the stimulation pulses.

The microcontroller 60 may further include timing control circuitry 79 which may be used to control timing of the stimulation pulses such as, e.g., pacing rate, atrio-ventricular (AV) delay, atrial interchamber (A—A) delay, and/or ventricular interchamber (V—V) delay. Such timing control circuitry 79 may also be used to keep track of the timing of refractory periods, noise detection windows, evoked response windows, alert intervals, marker channel timing, and so on.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, and the like) by selectively closing the appropriate combination of switches. Atrial sensing circuits 82 and ventricular sensing circuits 84 may also be selectively coupled to the right atrial lead 20, coronary sinus lead 24, and the right ventricular lead 30 through the switch 74, for detecting the presence of cardiac activity in each of the four chambers of the heart.

Accordingly, the atrial sensing circuit 82 and the ventricular sensing circuit 84 may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each of the atrial and ventricular sensing circuits 82, 84 preferably employs one or more low power, precision amplifiers with programmable gain, automatic gain or sensitivity control, band-pass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial sensing circuit 82 and ventricular sensing circuits 84 may be connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, may receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm may be physiologic or pathologic. As used herein, "sensing" generally refers to the process of noting an electrical signal, while "detection" generally refers to the step of confirming the sensed electrical signal as the signal being sought by the detector. As an example, "detection" applies to the detection of both proper rhythms (i.e., "P wave" or "R wave") as well as improper dysrhythmias including arrhythmia and bradycardia (e.g., detection of the absence of a proper rhythm).

The timing intervals between sensed events (e.g., P-waves, R-waves, and depolarization signals associated with fibrillation which are sometimes referred to as "F-waves" or "Fib-waves") are then classified by the arrhythmia detector 77 by comparing them to a predefined rate zone limit (e.g., bradycardia, normal, low rate ventricular tachycardia, high rate ventricular tachycardia, fibrillation rate zones, and so on) and various other characteristics (e.g., sudden onset, stability, physiologic sensors, morphology, and so on), in order to determine the type of remedial therapy required (e.g., bradycardia pacing, anti-tachycardia stimulation, cardioversion shocks or defibrillation shocks, collectively referred to as "tiered therapy").

Cardiac signals are also applied to the inputs of a data acquisition system 90 which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. Such a data acquisition system 90 may be coupled to the right atrial lead 20, the coronary sinus lead 24, and the right ventricular lead 30 through the switch 74 to sample the cardiac signals across any pair of desired electrodes.

Advantageously, such a data acquisition system 90 may be coupled to the microcontroller 60 and/or another detection circuitry, for detecting an evoked response from the heart 12 in response to an applied stimulus, thereby aiding in the detection of "capture." In the embodiment of FIG. 2, the microcontroller 60 may include an automatic capture detector 65 which searches for an evoked response signal following a stimulation pulse during a "detection window" set by timing control circuitry 79. The microcontroller 60 enables the data acquisition system 90 via control signal 92 to sample the cardiac signal which falls in the capture detection window. The sampled signal is evaluated by the automatic capture detector 65 to determine if it is an evoked response signal based on its amplitude, peak slope, morphology or another signal feature or combination of the features. Detecting the evoked response during the detection window may indicate that capture has occurred.

The microcontroller 60 may further be coupled to a memory 94 by a suitable data/address bus 96, wherein the programmable operating parameters used by the microcontroller 60 are stored and modified, as required, so as to customize the operation of the stimulation device 10 to suit the needs of particular patients. Such operating parameters may define, e.g., stimulation pulse amplitude, pulse duration, polarity of electrodes, rate, sensitivity, automatic features, arrhythmia detection criteria, and/or the amplitude, shape of waves, and/or vector of each stimulation pulse to be delivered to the patient's heart 12 within each respective tier of therapy.

The stimulation device 10 may additionally include a power source that may be illustrated as a battery 110 for providing operating power to all the circuits of FIG. 2. For the stimulation device 10 employing shocking therapy, the battery 110 must be capable of operating at low current drains for long periods of time, preferably less than 10 μA, and also be capable of providing high-current pulses when the patient requires a shock pulse, preferably in excess of 2 A, at voltages above 2 V, for periods of 10 seconds or more.

A patient warning signal generator is included in the microcontroller 60 such that a patient may be alerted to a condition that requires medical attention. A condition warranting a patient alarm may be related to the device 10 operation or may be related to a detected patient condition. For example, patient warning systems have been proposed for alerting a patient to a detected tachycardia and impending stimulation therapy delivery.

In accordance with one embodiment of the present invention, the patient warning generator is used to alert the patient to a low battery condition as will be described herein. Exemplary patient warning signals include a twitch sensation caused by delivery of a stimulation pulse or burst of pulses delivered to excitable tissue, or an audible warning sound.

As further illustrated in FIG. 2, the stimulation device 10 is shown to include an impedance measuring circuit 112 which is enabled by the microcontroller 60 by control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

Since stimulation device 10 is also intended to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118.

The shocking circuit 116 generates shocking pulses of low, moderate, or high energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted earlier, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
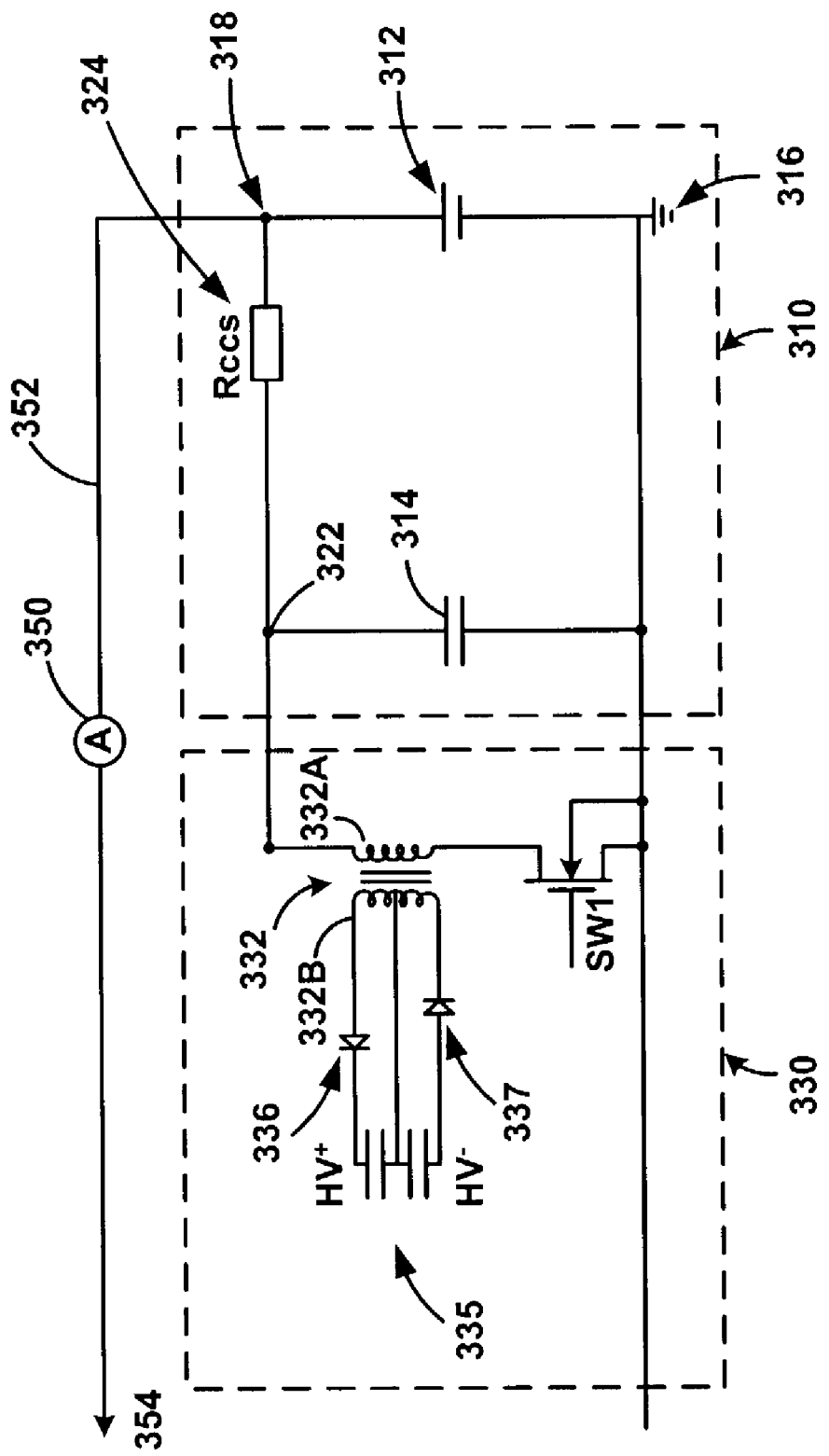
FIG. 3 is a circuit diagram of a shocking unit and a power supply unit of a prior art ICD.

FIG. 3 is a schematic diagram of a power supply unit 310 and a shocking unit 330 for a conventional ICD. The power supply unit 310 includes a primary power cell 312 and a decoupling capacitor 314, where the primary power cell 312 is connected between a ground node 316 and a first node 318, and where the decoupling capacitor 314 is connected between the ground node 316 and an output node 322. The ground node 316 is an artificial voltage reference within the device 10 and only weakly connected electrically to the device housing 40 that serves as a ground for the device 10. As such, the ground node 316 is in electrical contact with the patient's body in which the device 10 is implanted.

The weak connection between the housing 40 and the ground node 316 allows for amplifier noise rejection during sensing, and further allows the device housing 40 to be used as a high voltage electrode. The primary power cell 312 is typically arranged to provide the current flow required to charge a shock capacitor pair 335 used to store the charge for high voltage stimulation therapies. The power supply unit 310 further includes a charge current sense resistor ($R_{CCS}$) 324 connected between the first node 318 and the output node 322.

The shocking unit 330 is connected to the power supply unit 310 through an output node 322, and includes a DC-to-DC voltage converter 332 and an ON-OFF switch, $SW_1$. The voltage converter 332 typically includes two transformer coils. A first coil 332A receives an input pulse with low voltage and high current from the power cell 312. A second coil 332B generates an output pulse with high voltage and low current by electromagnetic induction by the flyback method.

The output shocking pulse is taken from the shock capacitor pair 335 by the shocking circuit 116 (of FIG. 2) and thereby applied to the patient's heart through at least two shocking electrodes selected from any of a left atrial coil electrode, a right ventricular coil electrode, and a SVC coil electrode. The housing 40 may act as an active electrode in combination with the right ventricular electrode, or as a part of a split electrical vector using the SVC coil electrode or the left atrial coil electrode.

Two diodes 336, 337 are disposed in an opposite polarities along the two leads of the second coil 332B of the DC-to-DC voltage converter 332, such that the high voltage output pulses (or shocking pulses) flow in only one direction (i.e., DC voltage). Diode 336 is connected to the positive terminal of capacitor pair 335, while diode 337 goes to the negative terminal. The middle line from the secondary coil 332B goes to the central terminal of the capacitor pair. The shock capacitor pair 335 preferentially has a voltage range of 600–900 V and a system capacitance range of 100–140 μF. Although detailed configurations and operational characteristics of the voltage converter 332 vary depending upon its applications, the voltage converter 332 is advantageously controlled by a microcontroller to generate shocking pulses of low energy (e.g., up to 0.5 joule), moderate energy (e.g., from 0.5 joule to 10 joules), or high energy (e.g., from 11 joules to 40 joules).

The switch $SW_1$ is connected between the ground node 316 and the first coil 332A of the voltage converter 332. The switch $SW_1$ is also coupled (or pulsed) to the microcontroller so that the shocking circuit 330 generates and delivers the shocking pulses to the patient's heart at desirable intervals or upon the occurrence of preset events. In general, the switch, $SW_1$, is a field effect transistor.

A first pathway 352 is provided between the first node 318 and a first input node 354 of the stimulation device, such that the power cell 312 can supply the electric current to the components of the stimulation device. A current sensing device 350 may be positioned along the first pathway 352 so that the microcontroller can detect the current supplied to components of the stimulation device. The current sensing device 350 may be a Hall effect sensor or a low-value resistor.

If the decoupling capacitor 314 becomes leaky, it may gradually drain the primary power cell 312. Accordingly, the ICD of the present invention are advantageously provided with various leakage detection systems that are arranged to prevent, or at least minimize current leakage or drainage by leaky electronic components of the stimulation device 10.

Figure 4:
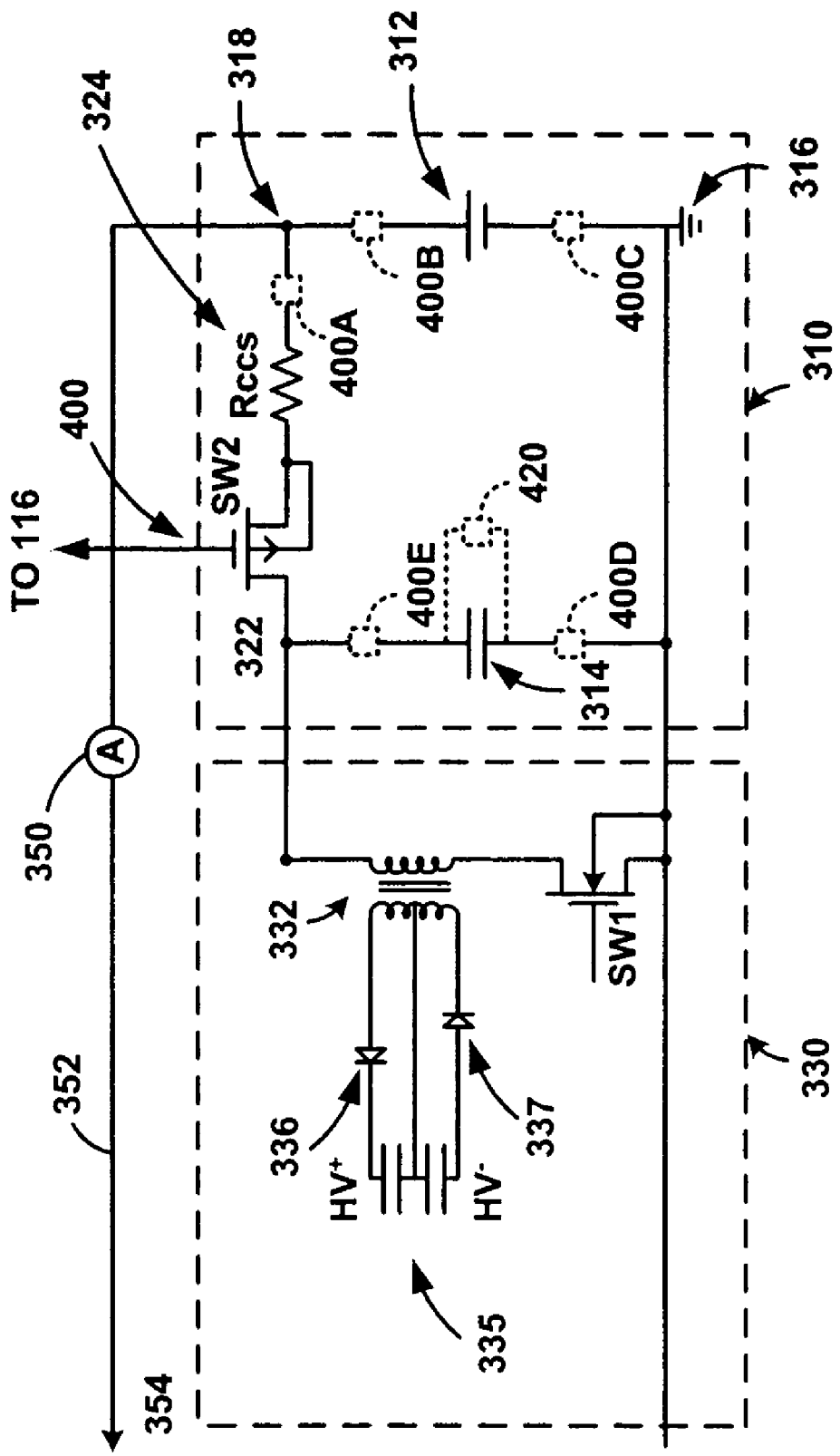
FIG. 4 is a circuit diagram of a leakage detection system capable of isolating a capacitor from a power cell according to the present invention.

FIG. 4 illustrates an exemplary leakage detection system 400 of the present invention, where an ON-OFF switch $SW_2$ is incorporated into a power supply unit 310, between the output node 322 and the resistor, $R_{CCS}$. The switch $SW_2$ is driven by the microcontroller 60 of FIG. 2, so that it opens and closes at preset instances, for preset (or programmable) periods, or upon the occurrence of preset events.

The switch $SW_2$ is preferably a field effect transistor with a very low ON resistance, for example on the order of tens of milliohms. The switch $SW_2$ may be an ON-chip switch, an OFF-chip switch, or an ON-OFF switch. It should be understood that the primary power cell 312 of FIG. 4 generally corresponds to the battery 110 of FIG. 2, while the shocking circuit 330 of FIG. 4 corresponds to the circuit 116 of FIG. 2.

In operation, the switch $SW_2$ is normally open and the primary power cell 312 is electrically isolated from the decoupling capacitor 314, so that no current flows through the power supply unit 310. In this state, the primary power cell 312 supplies electric current to other components of the stimulation device 10 like the sensors 82, 84, 108, memory 94, impedance measuring circuit 112, telemetry circuit 100, microcontroller 60, atrial pulse generator 70, and ventricular pulse generator 72, through the first current path 352, so that the device 10 performs its regular functions such as sensing, pacing, and other basic operations. Accordingly, possible current leakage through the leaky decoupling capacitor 314 can be entirely prevented while the stimulation device 10 is performing its regular functions. When desirable, the switch $SW_1$ can also be a normally open switch so that no current flows through the shocking unit 330.

As soon as a cardiac event, such as tachycardia, atrial fibrillation, or ventricular fibrillation is detected by the various sensors of the device 10, and the high-voltage shock pulses are required to be applied to the patient's heart for defibrillation or cardioversion, the microcontroller 60 activates the power supply unit 310 by closing the switch $SW_2$. The primary power cell 312 and the decoupling capacitor 314 then provide the desirable electric current through the output node 322.

The microcontroller 60 also pulses the switch $SW_1$ such that the shocking unit 330 can be activated for a preset period. For example, when the shock capacitor of the voltage converter 332 is charged by electromagnetic induction to the preset voltage, the microcontroller 60 controls the electrical configuration switch 74 to deliver the shocking pulses to the artial or ventricular electrodes 22, 23, 25–28, 32, 34, 36, 38 through corresponding leads 20, 24, 30.

When the sensors detect the termination of the tachycardia or defibrillation, the microcontroller 60 deactivates the shocking unit 330 and the power supply unit 310 by opening the switches $SW_1$ and $SW_2$. Thus, even though the decoupling capacitor 314 may leak, the amount of leakage current as well as the energy dissipated thereby may be maintained at a minimal level. The gates of SW1 and SW2 are connected to the microcontroller either directly or thru voltage level shifting circuits.

Modifications of the leakage detection system 400 of FIG. 4 also fall within the scope of the present invention. As an example, the switch $SW_2$ may be connected at other locations within the power supply unit 310, as indicated by the boxes 400A, 400B, 400C, 400D, and 400E, shown in dotted lines, such as between the resistor $R_{CCS}$ and the first node 318; between the first node 318 and the power cell 312; between the power cell 312 and the ground node 316; between the decoupling capacitor 314 and the ground node 316, and/or between the decoupling capacitor 314 and the node 322. The placement of the leakage detection system 400 (or its alternatives 400A, 400B, 400C, 400D, and 400E) is such that the power cell 312 can be selectively isolated from the capacitor 314 during the standard operation of the stimulation device 10, but connected to the capacitor 314 during high voltage shock operations.

In another aspect of the present invention, an exemplary leakage detection system 500 (FIG. 5) is provided by implementing multiple current paths through a shocking unit 570, and by including at least one switch along the current paths. The microcontroller 60 of the stimulation device 10 measures the voltage difference between the paths or the electric current from one path to another, analyzes the voltage and/or current, and detects the current leakage from a leaky component, such as the leaky decoupling capacitor 314.

Figure 5:
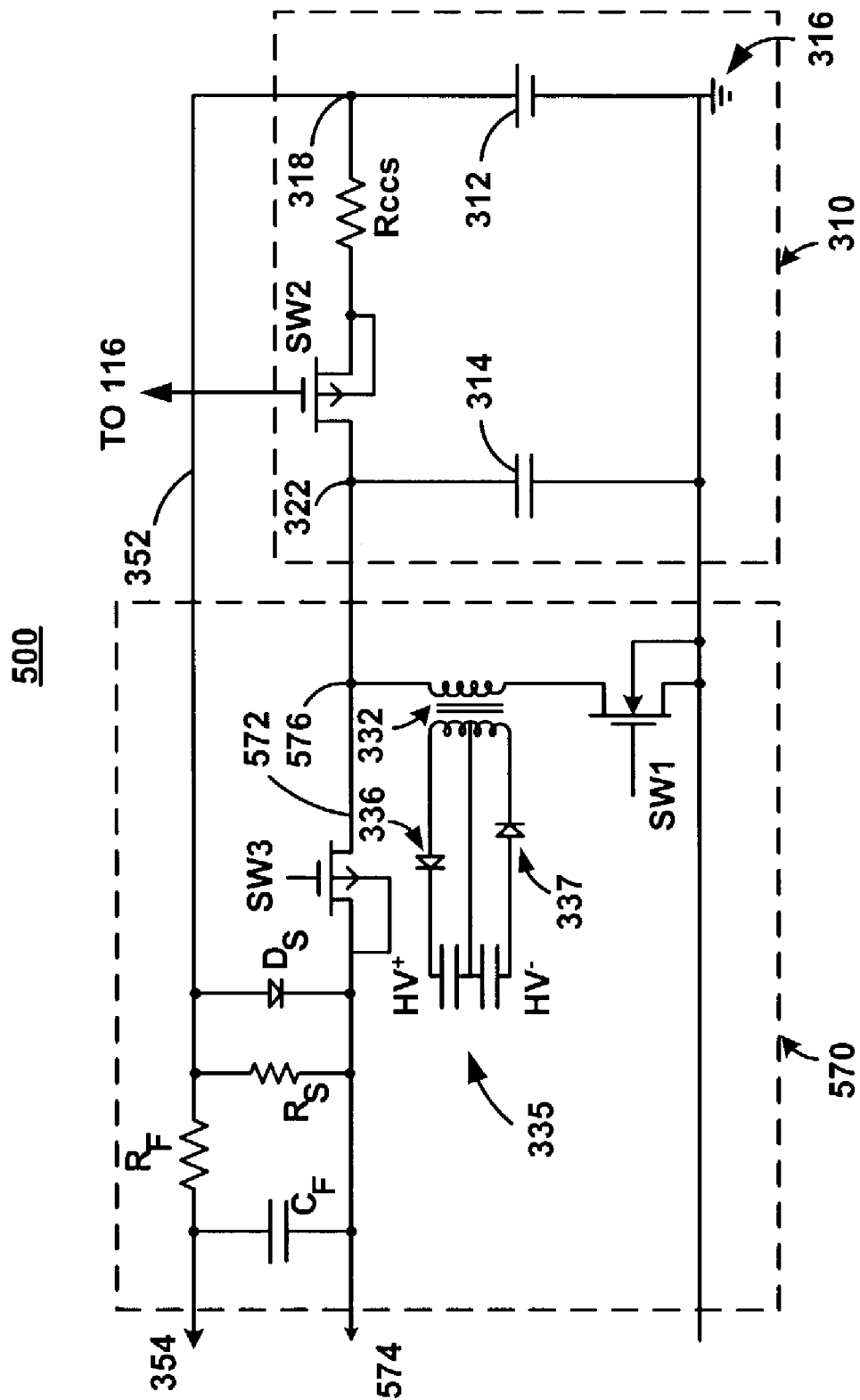
FIG. 5 is a circuit diagram of another leakage detection system for isolating a decoupling capacitor from a power cell according to the present invention.

FIG. 5 is a schematic diagram of the leakage detection system 500 for measuring the voltage or current, and for detecting current leakage from the decoupling capacitor 314 according to the present invention. The shocking unit 570 of the leakage detection system 500 includes the first path 352 that has been described earlier in conjunction with FIGS. 3 and 4, and a second current path 572 that extends from the output node 322 of the power supply unit 310 to a second input node 574.

In this exemplary embodiment, the second input node 574 is connected to the low voltage electronic components of the device 10, such as the monitoring and pacing circuitry. Thus, the power cell 312 provides the electric current to the electronic components through the second path 572, while the remaining components of the stimulation device 10 are supplied with an electric current through the first path 352.

Along the second current path 572, the shocking unit 570 includes an ON-OFF switch $SW_3$ to enable the second path 572 to be selectively opened or closed. The ON-OFF switch $SW_3$ is disposed between the second input node 574 and a second node 576 of the shocking unit 570, but not between the shocking unit 570 and the power supply unit 310. Accordingly, opening the switch $SW_3$ does not necessarily deactivate the entire shocking unit 570.

Similar to switches $SW_1$ and $SW_2$ of FIG. 4, switch $SW_3$ is also driven by the microcontroller 60 so that it opens and closes at preset instances, for preset periods, and/or upon the occurrence of preset events. The switch $SW_3$ is preferably a field effect transistor (FET) whose ON-resistance is on the order of a few ohms.

The first and second current paths 352, 572 may be connected by electronic components, such as a sensing resistor ($R_S$) that allows measurement of the voltage between the two paths 352, 572, or the current therethrough. As it will be described below and depending upon the activation status of the switches $SW_2$ and $SW_3$, the resistor ($R_S$) allows the measurement of the total electric current to the electronic components or to the entire circuitry of the stimulation device 10 including any leakage by the decoupling capacitor 314.

A diode ($D_S$) may also be connected between the first and second paths 352, 572 to allow the flow of current only from the first path 572 to the second path 352, and to provide in-rush currents for avoiding power supply sagging at power-up of the stimulation device 10. The shocking unit 570 may also include a capacitor ($C_F$) connected between the first and second current paths 352, 572, and a resistor ($R_F$) disposed along the first (or second) path 352. In general, the resistor ($R_F$) and capacitor ($C_F$) are designed to reduce noise by low pass filtering.

In operation, all three switches $SW_1$, $SW_2$, and $SW_3$ are normally open and both of the power supply unit 310 and the shocking unit 570 are deactivated. Accordingly, the primary power cell 312 is electrically isolated from the decoupling capacitor 314 and no electric current flows through any of the power supply unit 310 or the shocking unit 570. In this state, the primary power cell 312 supplies the electric current to other components of the stimulation device 10, such as the sensors 82, 84, 108, the memory 94, the impedance measuring circuit 112, the telemetry circuit 100, the microcontroller 60, and/or the atrial pulse generator 70, through the first current path 352. Accordingly, the device 10 can perform its primary functions such as sensing and pacing operations, while preventing possible current leakage through the leaky decoupling capacitor 314 or through the shock capacitor of the shocking unit 570.

The leakage detection system 500 of FIG. 5 also allows the detection of the current leakage from the decoupling capacitor 314. For example, when both switches $SW_2$ and $SW_3$ are open, the voltage across the resistor ($R_S$) is at least substantially proportional to the total electric current flowing to the electronic components of the stimulation device 10. Accordingly, the microcontroller 60 compares the measured voltage to a preset voltage value or range and flags a warning signal when the measured voltage is found to be outside the normal operating range.

When tachycardia, atrial fibrillation, or ventricular fibrillation is detected and high-voltage shock pulses need to be applied to the patient's heart for defibrillation and/or cardioversion, the microcontroller 60 activates the power supply unit 310 by closing the switch $SW_2$. The primary power cell 312 and the decoupling capacitor 314 provide the desired electric current along the power supply unit 310 and through the output node 322. The microcontroller 60 also closes the switch $SW_3$ to provide the electric current from the power supply unit 310 to the shocking unit 570 via the output node 322, thereby activating the shocking unit 570.

When the shock capacitor of the voltage converter 332 is charged to a preselected voltage by electromagnetic induction, the microcontroller 60 pulses the switch $SW_1$ and regulates the electrical configuration switch 74 to deliver high voltage shocking pulses to the artial and/or ventricular electrodes 22, 23, 25–28, 32, 34, 36, 38 through the corresponding electrical leads 20, 24, 30. When the sensors detect the termination of the dysfunction condition, the microcontroller 60 deactivates the shocking unit 570 and the power supply units 310 by opening the switches $SW_2$ and $SW_3$ (and $SW_1$ when desirable). Therefore, even though the decoupling capacitor 314 and the shock capacitor may leak, the amount of leakage current and the energy dissipated thereby can be maintained at a minimal level.

The leakage detection system of FIG. 5 allows another means for detecting the leakage of current from the decoupling capacitor 314. For example, when the switch $SW_2$, is open but the switch $SW_3$ is closed, the voltage across the resistor ($R_S$) becomes at least substantially proportional to the total electric current flowing to other components of the stimulation device 10. Accordingly, the microcontroller 60 compares the measured voltage to a preset voltage value or range and flags a warning signal when the voltage is found to be outside the normal operating range.

Modifications of the foregoing leakage prevention and detection system 500 of FIG. 5 also fall within the scope of the present invention. For example, switch $SW_3$ may be disposed at other locations along the second current path 572 such as between the filtering capacitor ($C_F$) and sensing resistor ($R_S$), between the resistor ($R_S$) and diode ($D_S$). In addition, sensors may be incorporated along the second current path 572 of the shocking unit 570, in particular across the sensing resistor ($R_S$) to measure the voltage thereacross and/or the current therethrough. The microcontroller 60 may also be arranged to coordinate the operations of the switches, $SW_1$, $SW_2$, and $SW_3$ so that two or all of these switches may be opened or closed based, not only on the operating characteristics of the stimulation device 10, but also based on the presence of the current leakage through the decoupling capacitor 314 or other leaky components.

The leakage detection systems of the present invention aim to prevent or minimize the current leakage by isolating the power cells from leaky components. While detailed descriptions of the specific embodiments of the leakage detection systems have been provided, it should be apparent to those skilled in the art that other variations of these systems are possible without departing from the scope of the present invention. The descriptions provided herein are for the sake of illustration and are not intended to be exclusive.

What is claimed is:

1. A cardiac stimulation device operative to apply a high-voltage shock to a heart, said device comprising:
   a voltage converter having an input side and an output side;
   a high voltage capacitor coupled to the output side for delivering the high-voltage shock;
   a decoupling capacitor coupled to the input side, the decoupling capacitor for charging the high voltage capacitor through the voltage converter;
   a power cell coupled to the decoupling capacitor through a switch; and
   a controller operative to detect current leakage from the decoupling capacitor and to control the switch to disconnect the decoupling capacitor from the power cell when leakage is detected and the decoupling capacitor is not charging the high voltage capacitor.

2. The device of claim 1 wherein the power cell and the decoupling capacitor are coupled in parallel.

3. The device of claim 1 wherein the decoupling capacitor and the input side of the voltage converter are coupled in parallel.

4. The device of claim 1 wherein the switch comprises a transistor.

5. The device of claim 1 wherein the controller comprises a sensor coupled in parallel with the decoupling capacitor, for detecting leakage current.

6. The device of claim 1 wherein the power cell and the decoupling capacitor are connected to ground and the switch is positioned between one of the power cell and ground or the decoupling capacitor and ground.

7. A method for use in a cardiac stimulation device operative to apply a high-voltage shock to a heart, the device having a voltage converter with an input side and an output side, a high voltage capacitor coupled to the output side for delivering the high-voltage shock, a decoupling capacitor coupled to the input side, the decoupling capacitor for charging the high voltage capacitor through the voltage converter, and a power cell coupled to the decoupling capacitor through a switch, said method comprising:

detecting current leakage from the decoupling capacitor; and opening the switch to disconnect the decoupling capacitor from the power cell when leakage is detected and the decoupling capacitor is not charging the high voltage capacitor.

8. A cardiac stimulation device having low-voltage operations and high-voltage operations, said device comprising:

a voltage converter having an input side and an output side;

a high voltage capacitor coupled to the output side for delivering a high-voltage shock during high-voltage operations;

a decoupling capacitor coupled to input side, the decoupling capacitor for charging the high voltage capacitor through the voltage converter;

a power cell coupled to the decoupling capacitor through a switch; and a controller operative to detect current leakage from the decoupling capacitor and to control the switch such that it is closed only during high-voltage operations.

\* \* \* \* \*

UNITED STATES PATENT AND TRADEMARK OFFICE
CERTIFICATE OF CORRECTION

| | | |
|---|---|---|
| PATENT NO. | : 7,158,825 B1 | Page 1 of 1 |
| APPLICATION NO. | : 10/373236 | |
| DATED | : January 2, 2007 | |
| INVENTOR(S) | : Mark W. Kroll, Gabriel A. Mouchawar and George I. Isaac | |

It is certified that error appears in the above-identified patent and that said Letters Patent is hereby corrected as shown below:

On Title page Item (75), please delete "Geroge" and insert --George--.

Signed and Sealed this

Twenty-seventh Day of March, 2007

JON W. DUDAS
*Director of the United States Patent and Trademark Office*